(12) United States Patent
Haluck (10) Patent No.: US 6,685,724 B1
(45) Date of Patent: Feb. 3, 2004

(54) LAPAROSCOPIC SURGICAL INSTRUMENT AND METHOD

(75) Inventor: Randy S. Haluck, Hershey, PA (US)

(73) Assignee: The Penn State Research Foundation, University Park, PA (US)

( * ) Notice: Subject to any disclaimer, the term of this patent is extended or adjusted under 35 U.S.C. 154(b) by 226 days.

(21) Appl. No.: 09/644,011

(22) Filed: Aug. 22, 2000

Related U.S. Application Data (60) Provisional application No. 60/150,613, filed on Aug. 24, 1999.

(51) Int. Cl.[7] ............................................... A61B 17/28
(52) U.S. Cl. ...................................................... 606/207
(58) Field of Search ............................. 606/207, 205, 606/206, 209, 210, 185; 604/264, 164, 139

(56) References Cited

U.S. PATENT DOCUMENTS

| | | | |
|---|---|---|---|
| 5,256,149 A | 10/1993 | Banik et al. | 604/164 |
| 5,318,589 A | 6/1994 | Lichtman | 606/205 |
| 5,330,437 A | 7/1994 | Durman | 604/167 |
| 5,380,288 A | 1/1995 | Hart et al. | 604/167 |
| 5,387,197 A | 2/1995 | Smith et al. | 604/164 |
| 5,476,479 A | * 12/1995 | Green et al. | 606/207 |
| 5,509,923 A | * 4/1996 | Middleman et al. | 606/170 |
| 5,575,805 A | 11/1996 | Li | 606/206 |
| 5,609,604 A | 3/1997 | Schwemberger et al. | 606/185 |
| 5,776,112 A | 7/1998 | Stephens et al. | 604/264 |
| 5,797,958 A | 8/1998 | Yoon | 606/207 |
| 5,817,061 A | 10/1998 | Goodwin et al. | 604/164 |
| 5,836,960 A | 11/1998 | Kolesa et al. | 606/170 |
| 5,857,999 A | 1/1999 | Quick et al. | 604/107 |
| 6,001,120 A | * 12/1999 | Levin | 606/207 |

* cited by examiner

*Primary Examiner*—Kevin T. Truong
(74) *Attorney, Agent, or Firm*—McKee, Voorhees & Sease, P.L.C.

(57) ABSTRACT

A surgical instrument is provided for use in performing endoscopic procedures having a handle and an elongate tubular member having a proximal end coupled with the handle for being disposed externally of the anatomical cavity and a distal end for being disposed within the anatomical cavity. The distal end further includes a pair of opposed, relatively movable jaws that form a grasping portion operable by manipulation of the handle to releasably grasp a releasable trocar. The releasable trocar has a complementarily shaped shank, a relatively sharp tip and may include a pair of blunt-edge tissue separators that project outwardly from the outer surface of the trocar. In an alternative embodiment, the relatively movable jaws define (i) a grasping portion operable by manipulation of the handle to grasp or cut objects; and (ii) a pair of blunt-edge tissue separators that project outwardly from the outer surface of the jaws so that when the jaws are in a closed position they may be used as a trocar. In another embodiment, a portal tube is sealingly positioned on the elongate tubular member and is operative to move between (i) a first position in which the portal is in a proximal location on the elongate tubular member and in spaced relation to the anatomical cavity, and (ii) a second position in which the portal is in a distal location on the elongate tubular member and in sealed communication with said anatomical cavity. The optional portal may be used with either the releasable trocar or the jaw trocar. A method for using the surgical instrument is also provided.

16 Claims, 6 Drawing Sheets

LAPAROSCOPIC SURGICAL INSTRUMENT AND METHOD

This application claims the benefit of provisional application Ser. No. 60/150,613 filed Aug. 24, 1999.

FIELD OF THE INVENTION

The present invention relates generally to medical instruments and procedures and more particularly, to an instrument for use in laparoscopic or endoscopic surgical procedures.

BACKGROUND OF THE INVENTION

Endoscopic and minimally invasive medical procedures, such as laparoscopy, have become widely accepted for surgery and illness diagnosis. This is due to reduced trauma to the patient and reduced hospitalization time. Other techniques exist for creating a working space within the abdominal cavity, but the vast majority of laparoscopic operations worldwide are performed using the technique of pneumoperitoneum.

At the beginning of all laparoscopic cases, a small incision is made, followed by a small (1 cm) hole in the remaining layers of the abdominal wall so as to gain access to the peritoneal cavity. An alternative method of gaining access to the peritoneal cavity is to insert a small needle through the abdominal wall and to instill $CO_2$ through this needle into the peritoneal cavity. The peritoneal cavity is usually inflated to a pressure of about 14 cm $H_2O$. The pressure of the pneumoperitoneum must be maintained at all times during the operation. An automatic insufflation pump keeps $CO_2$ flowing to maintain a preset working pressure. If pressure is lost, the working space collapses, nothing can be seen, via a video system, and the operation comes to a halt. This working pressure must be maintained despite the need to introduce and remove cameras, instrumentation, and the like through the abdominal wall during the operation.

The solution to this problem has been the development of laparoscopic ports. These devices, in their simplest form, consist of tubes which penetrate the abdominal wall to provide a path for the introduction, removal, and exchange of instruments, etc. Prior art ports must be inserted through the abdominal wall. This is usually done by the use of a sharp spike, known in the art as a "trocar," which is positioned within the lumen of the port, and inserted into the abdominal wall so as to pierce it. The trocar is then removed from the lumen of the port. Prior art ports also incorporate some type of valve or seal mechanism to create an airtight seal around an instrument as it is slid through the port and into the abdominal cavity. This is to prevent leakage from the pressurized pneumoperitoneum. The seals must be efficient, as even seemingly small leaks can exceed the maximum insufflation rate of $CO_2$ pump.

Most laparoscopic operations use pneumoperitoneum and a separate port of each instrument. For example, for gallbladder removal (laparoscopic cholecystectomy), two instruments are required for retraction, while another is required for dissection, then often requiring three ports. An additional port is required for the video camera bringing the total number of ports required to four for performing a laparoscopic cholecystectomy. Instruments may be exchanged through any of the ports at any time. Other common laparoscopic operations including hernia repair, appendectomy, stomach surgery, and gynecologic surgery require from three to five ports for performing each operation. Such procedures commonly involve performing a number of individual acts or functions within the anatomical cavity including grasping, cutting, coagulating, irrigating, aspirating, puncturing, injecting, dissecting, cauterizing, ligating, suturing, illuminating, visualizing and/or collection specimens for biopsy. Endoscopic instruments are often designed to perform only one of the above functions, requiring several incisions for placement of multiple portals to accommodate a suitable number of endoscopic instruments for performing the required functions or necessitating frequent withdrawal and replacement of the individual endoscopic instruments through a single incision. In some instances, an endoscopic instrument may be inserted into the abdomen of the patient and not removed until the procedure is completed. Here, no instrument exchange is required, even though a port is in place.

The majority of laparoscopic ports used are disposable. Reusable, sterilizable ports are available, but have several drawbacks. In order to purchase sufficient reusable ports to accommodate a moderate sized operating room facility several thousands of dollars in capital expenditure is required by the hospital. Known reusable ports are also somewhat difficult to maintain. Rubber seals and valves crack and break with repeated use and sterilization. Maintaining and replacing small seals and parts requiring disassembly of the port is tedious and often results in lost or damaged parts. Also, the trocar portion of the apparatus often becomes dull after several uses. Using a port that is not sharp, or that leaks is frustrating for the surgeon and potentially dangerous to the patient.

SUMMARY OF THE INVENTION

In one embodiment of present invention, a surgical instrument for use in performing endoscopic procedures within an anatomical cavity is provided comprising a handle and an elongate member having a proximal end coupled with the handle for being disposed externally of the anatomical cavity and a distal end for being disposed within the anatomical cavity. The distal end further includes a pair of opposed, relatively movable jaws that form a grasping portion operable by manipulation of the handle to releasably grasp a releasable trocar. The releasable trocar comprises a shank that is adapted for grasping, a relatively sharp tip and may include a pair of blunt-edge tissue separators that project outwardly from the outer surface of the trocar.

In an alternative embodiment, the relatively movable jaws define (i) a grasping portion operable by manipulation of the handle to grasp; and (ii) a pair of blunt-edge tissue separators that project outwardly from the outer surface of the jaws so that when the jaws are in a closed position they may be used for tissue penetration.

In another alternative embodiment of the invention, a portal tube is sealingly positioned on the elongate member and is operative to move between (i) a first position in which the portal is in a proximal location on the elongate member and in spaced relation to the anatomical cavity, and (ii) a second position in which the portal is in a distal location on the elongate member and in sealed communication with said anatomical cavity.

In a further embodiment of the invention the optional portal may be used with either the releasable trocar or the jaw trocar.

A method is provided for gaining access to an anatomical cavity comprising the steps of providing a surgical instrument formed according to any one of the foregoing embodiments of the invention. Manipulating the handles of the instrument so as to close the jaws, and then pressing the jaws against the tissue of the wall of the anatomical cavity so as to separate the tissue. The jaws are then moved to an operative site within the anatomical cavity. The foregoing method may include the step of positioning a portal between the separated tissue while maintaining the jaws at the operative site, andmay also be performed with either the releasable trocar or the jaws having a pair of blunt-edge tissue separators.

BRIEF DESCRIPTION OF THE DRAWINGS

These and other features and advantages of the present invention will be more fully disclosed in, or rendered obvious by, the following detailed description of the preferred embodiments of the invention, which are to be considered together with the accompanying drawings wherein like numbers refer to like parts and further wherein.

DETAILED DESCRIPTION OF THE PREFERRED EMBODIMENT

The following description of the preferred embodiments of the invention are intended to be read in connection with the foregoing drawings and are to be considered a portion of the entire written description of this invention. As used in the following description, terms such as, "horizonal", "vertical", "left", "right", "up", and "down", as well as adjectival and adverbial derivatives thereof (e.g., "horizontally", "rightwardly", "upwardly", etc.) simply refer to the orientation of the structure of the invention as it is illustrated in the particular drawing figure when that figure faces the reader. Similarly, the terms "inwardly" and "outwardly" generally refer to the orientation of a surface relative to its axis of elongation, or axis of rotation, as appropriate. Also, the terms such as "connected" and "interconnected," when used in this disclosure to describe the relationship between two or more structures, means that such structures are secured or attached to each other either directly or indirectly through intervening structures, and includes pivotal connections. The term "operatively connected" means that the foregoing direct or indirect connection between the structures allows such structures to operate as intended by virtue of such connection.

The endoscopic instrument of the present invention can be utilized in any type of anatomical cavity. Accordingly, while the invention is described hereinafter for use with laparoscopy procedures, the invention can be used with catheters and other small or large diameter tubular or hollow, cylindrical members providing access to small cavities, such as veins and arteries as well as large cavities, such as the abdomen.

Figure 1:
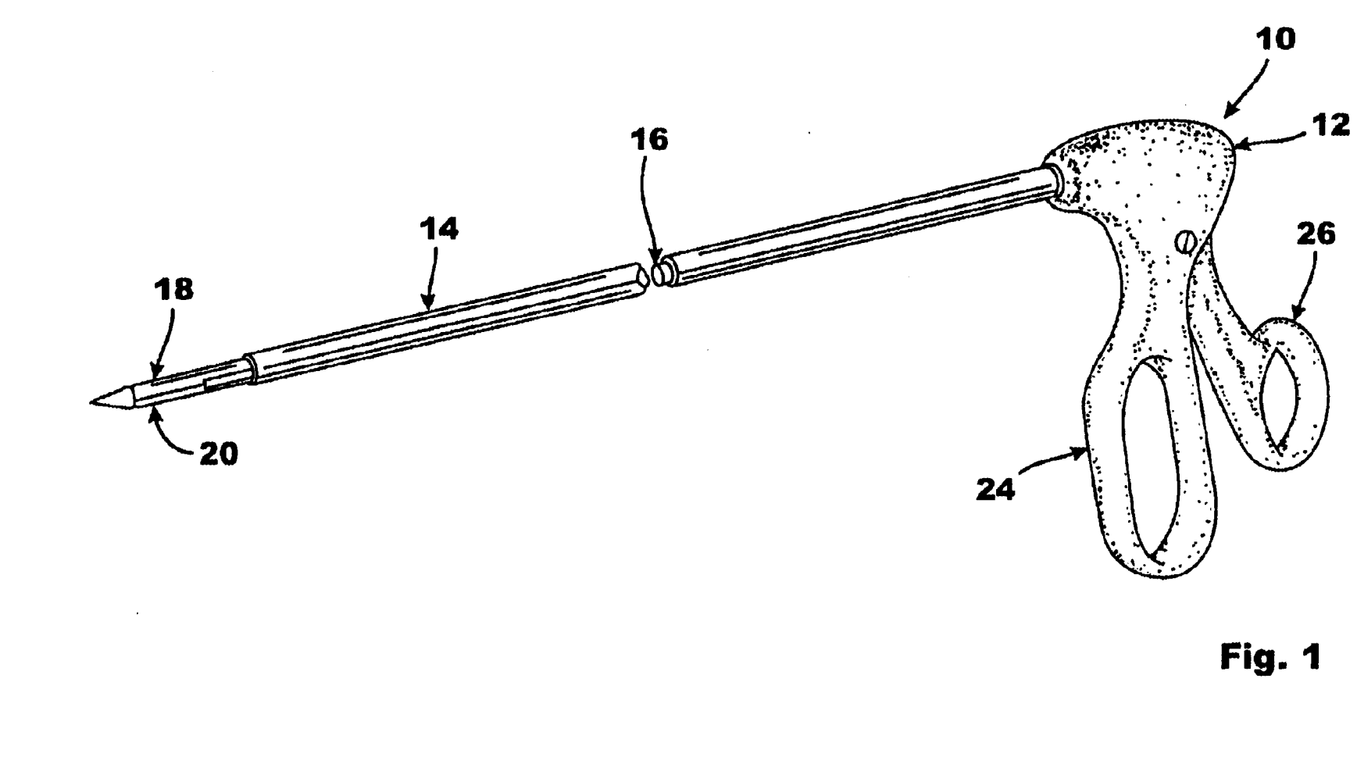
FIG. 1 is a perspective view an endoscopic instrument according to one embodiment of the present invention.
Figure 2:
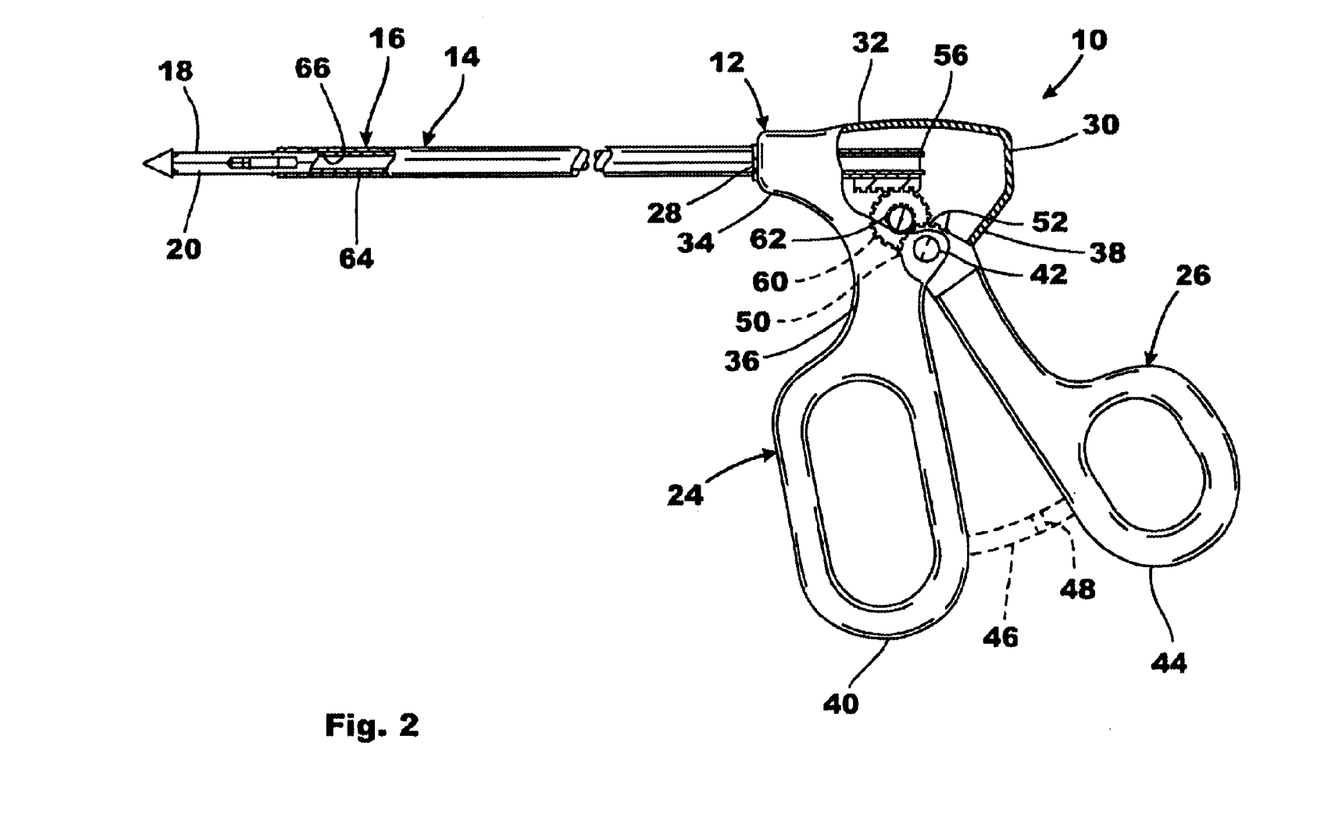
FIG. 2 is a partially broken away, elevational view of the endoscopic instrument shown in FIG. 1.
Figure 3:
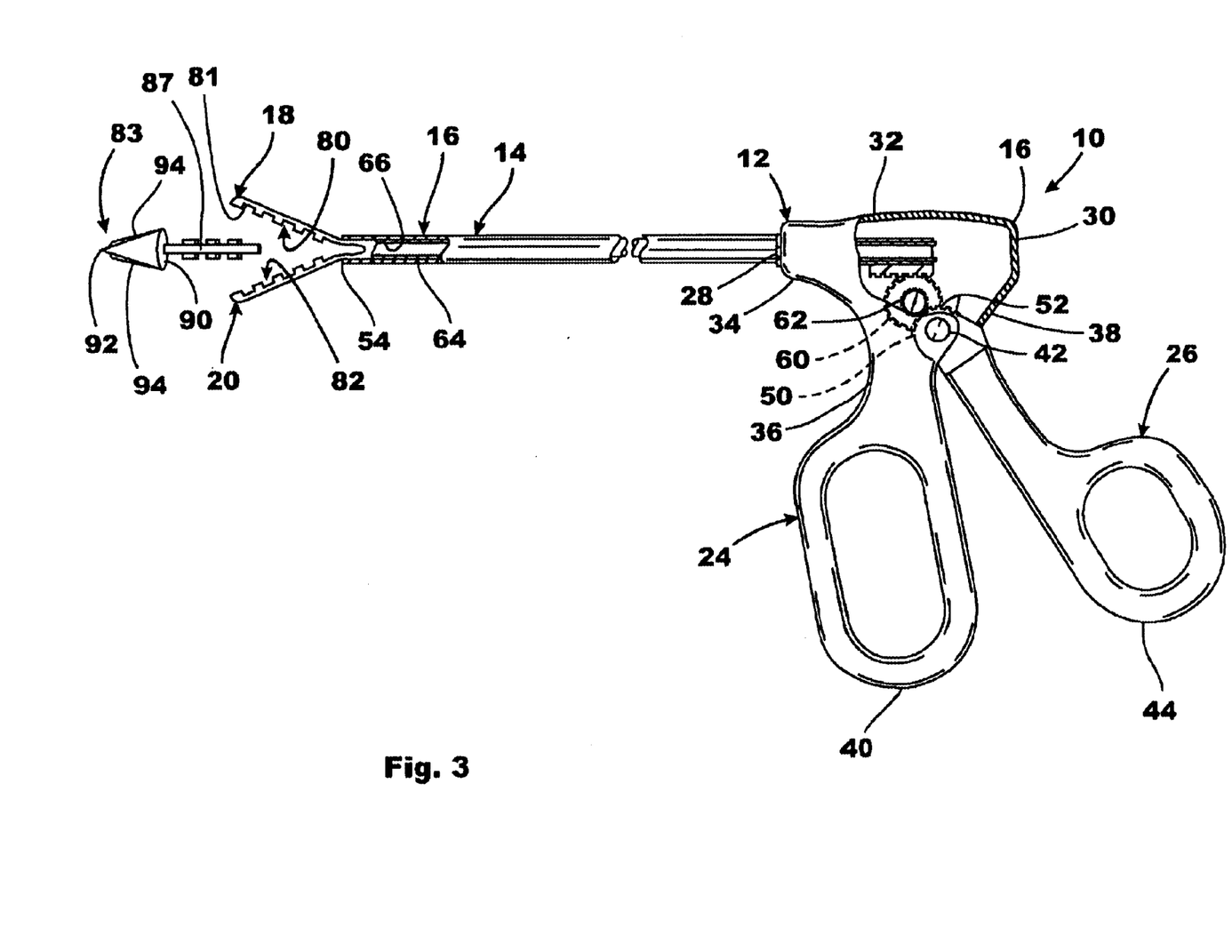
FIG. 3 is a partially broken away, elevational view of the endoscopic instrument shown in FIG. 1, showing a graspable trocar bit just prior to engagement with the jaws of the instrument.

Referring to FIGS. 1–3, an endoscopic instrument 10 formed in accordance with the present invention, includes a housing 12, an outer tubular member 14 extending distally from the housing 12, an inner tubular member 16 telescopically fitted within the outer tubular member and terminating distally in a pair of opposed jaws 18 and 20, and a handle portion formed of a fixed handle 24 and a movable handle 26.

More particularly, housing 12 includes longitudinally spaced front and rear walls 28 and 30 that are oriented perpendicular to a longitudinal axis of endoscopic instrument 10. A top wall 32 is disposed in substantially parallel relation to the longitudinal axis. A bottom wall 34 includes a concave forward portion 36 that curves downwardly from front wall 28 to connect with an upper end of fixed handle 24. A rearward portion 38 of housing 12 extends proximally at an angle relative to the longitudinal axis of endoscopic instrument 10 from an upper end of handle 24 to rear wall 30. A lower end of fixed handle 24 is configured as an elongate finger loop 40 to accommodate one or more fingers of a user. Movable handle 26 is pivotally mounted on a pin 42 proximally spaced from fixed handle 24 and secured internally to a wall or walls of housing 12. A lower end of handle 26 is configured as a finger loop 44 to accommodate one or more fingers of the user, and a pair of arcuate mating protrusions, shown by broken lines at 46 and 48 in FIG. 2, can optionally be carried in opposed relation on finger loops 40 and 44 for ratcheting engagement during use. Movable handle 26 includes an arcuate end portion 50 disposed within housing 12 and defining a plurality of gear teeth 52 on a side of pin 42 opposite finger loop 44.

Outer tubular member 14 is open at both ends and extends distally from housing 12 through an opening in front wall 28. Distal end 54 of outer tubular member 14 can be blunt as shown, tapered, beveled, slotted or chamfered as desired or have any other suitable distal configuration. Preferably, outer tubular member 14 comprises a cylindrical cross-section along its length, and is formed from a substantially rigid material, such as stainless steel or other biocompatible metal or polymer material. Proximal end 56 of outer tubular member 14 is movably disposed within housing 12, and carries a rack 58 in spaced relation to toothed end portion 50 of handle 26. A pinion gear 60 engages rack 58, and is mounted on the same shaft as a reduction gear 62 which meshingly engages toothed end portion 50 of handle 12 to convert relatively small rotary or pivotal movement of handle 12 into significantly larger linear movement of rack 58.

It will be appreciated that counterclockwise rotation of handle 26 about pin 42 results in proximal movement of outer tubular member 14 relative to housing 12 and that clockwise rotation of handle 26 about pin 42 results in distal movement of outer tubular member 14 relative to housing 12. In a preferred embodiment, movable handle 26 is biased in a clockwise direction toward fixed handle 24, for example by use of a torsion spring (not shown) coiled around pin 42 and connected between movable handle 26 and fixed handle 24 and/or housing 12.

The handle portion of the endoscopic instrument shown and described herein is exemplary of the types of conventional handle mechanisms suitable for performing the function of actuating the jaws; accordingly, the handles can have any configuration to actuate the jaws including, but not limited to, configurations employing a pair of pivotally connected arms, one fixed and one pivoted arm, a pistol grip with a movable trigger, or resilient U-shaped handle members. Further, the handle portion of the instrument can be configured to rotate relative to a pivot axis oriented perpendicular to the longitudinal axis of the instrument so that, for example, in one position the handles will extend laterally from the instrument or at a substantially perpendicular angle relative to the longitudinal axis; while, in another position, the handles will extend proximally from the instrument like scissor handles.

Inner member 16 includes a tubular portion 64 telescopically fitted within outer tubular member 14, and defining a lumen or channel 66 through endoscopic instrument 10. The proximal end of inner member 16 extends through the proximal end of outer tubular member 14 within housing 12. The distal end of tubular portion 64 is bifurcated or split longitudinally to form integral one-piece jaws 18 and 20 in opposed relation, the jaws being normally biased apart as shown in FIG. 3. Tubular body 64 is preferably formed with jaws 18 and 20 as a single unitary part using a resilient biocompatible material such as, for example, a spring steel or an elastomeric polymer material having suitable elastic properties for normally biasing the upper and lower jaws apart while permitting the jaws to be moved toward one another in response to forces acting on the outer jaw surfaces and/or cams as a result of relative axial movement between outer tubular member 14 and inner member 16.

In the first embodiment of the present invention, jaws 18 and 20 cooperate to define a grasping portion at a distal end having opposed inner surfaces 80 and 82. Jaws 18 and 20 include means 81 for grasping a releasable trocar 83. More particularly, grasping means 81 may include a combination of indentation recess, protrusions or teeth that are arranged for securely holding releasable trocar 82 when closed. Releasable trocar 83 preferably comprises a conical profile to facilitate the penetration or dissection of tissue, and includes a shank 87, a base 90, and an apex 92. Shank 87 comprises a relatively elongate shaft that projects outwardly from the center portion of base 90, and includes a series of indentations, recesses, protrusions or teeth that are arranged in a complementary pattern corresponding to opposed inner surfaces 80 and 82 of jaws 18 and 20. Base 90 has a diameter substantially equivalent to that of inner member 16. Apex 92 is pointed so as to be capable of piercing or separating tissue without inflicting severe trauma. In some cases, a pair of blunt-edged blades 94, or tissue separators, are positioned on the outer conical surface of trocar 83. Blunt-edged blades 94 are arranged in circumferentially spaced relation to one another, and project outwardly from the conical surface of trocar 83 to facilitate the penetration.

Instrument 10 is used in connection with the foregoing first embodiment of the invention in the following manner. Since inner member 16 is fixed relative to housing 12 actuation of jaws 18 and 20 is controlled by moving outer tubular member 14 relative to inner member 16. If closed, jaws 18 and 20 can be opened by moving outer tubular member 14 proximally relative to inner member 16. Movement of outer tubular member 14 over inner member 16 is controlled by operation of movable handle 26. Counterclockwise rotation of handle 26 about pin 42 results in clockwise rotation of reduction gear 62 which, in turn, causes an equal angular rotation of pinion 60. Pinion 60 is of greater diameter than reduction gear 62 so that, for equal angles of rotation, pinion 60 will produce greater circumferential displacement. Pinion 60 engages the gear teeth of rack 58 to cause proximal movement of outer tubular member 14 relative to jaws 18 and 20 thereby permitting the jaws to move resiliently to the open position, shown in FIG. 3. In the open position, jaws 18 and 20 are biased apart such that grasping means 81 are angularly spaced from one another allowing shank 87 of trocar 83 to be positioned between jaws 18 and 20. Clockwise rotation of handle 26 about pin 42 results in counterclockwise rotation of reduction gear 62 and pinion 60 causing distal movement of rack 58 and outer tubular member 14 relative to the jaws so that distal end 54 of outer tubular member 14 will slide over the jaws in an axial direction causing the jaws to be cammed inwardly from the open position to a closed position. As the jaws move from the open position to the closed position, grasping means 81 rotate toward one another to grasp shank 87. More particularly, the complementary indentations, recesses, protrusions or teeth engage one another to securely clamp trocar 83 between jaws 18 and 20. It will be understood that arcuate mating protrusions 46 and 48 latched together to maintain handle 26 in position related to fixed handle 24, and thereby maintain jaws 18 and 20 in gripping relation with shank 87 of trocar 83.

Once trocar 83 is installed, instrument 10 may be guided, by hand, to the wall of an anatomical cavity. Instrument 10 is advanced distally through the abdominal wall with jaws 18 and 20 disposed in a tightly closed configuration around shank 87 of trocar 83. Once the abdominal wall has been pierced by trocar 83, the instrument can be manipulated externally of the body to position the jaws so that trocar 83 may be released and removed from the operative site, via a retrieval tool that has been positioned within the abdomen through a portal. Various grasping and cutting functions can be performed at the operative site using different tools that have been affixed to jaws 18 and 20, via a similarly arranged shank 87, and by operating the handles of the instrument to open and close the jaws as required.

Movable handle 26 is preferably proximally spaced from fixed handle 24 as shown so that the user can maintain one or more fingers on the stationary handle 24 while operating the movable handle 26 with the thumb and/or other fingers of the hand. Movable handle 26 is preferably biased in a clockwise direction, looking at FIG. 3, toward stationary handle 24 so that, when the movable handle is released, outer tubular member 14 will be automatically moved over jaws 18 and 20 to close the jaws together to hold trocar 83 between the jaws.

Figure 4:
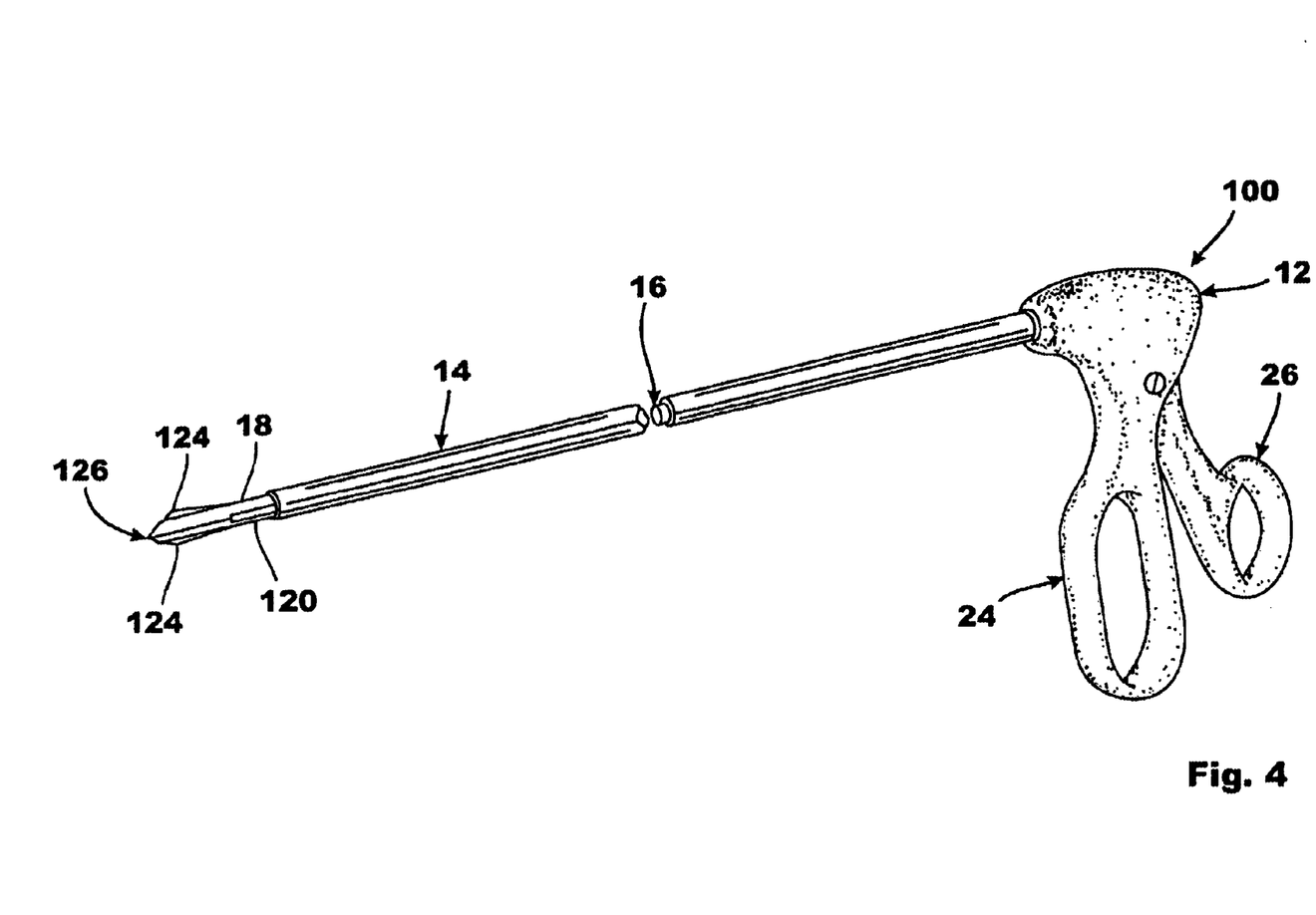
FIG. 4 is a perspective view of an endoscopic instrument according to an alternative embodiment of the present invention.

Referring to FIG. 4 in an alternative embodiment of the present invention an instrument 100 is provided with a pair of jaws 118 and 120 comprising a pair of blunt-edged blades 124, or tissue separators, that are positioned on the outer surface of jaws 118 and 120. Blunt-edged blades 124 are arranged in circumferentially spaced relation to one another, and project outwardly from the outer surface of each jaw 118 and 120. The respective tip portion 126 of jaws 118 and 120 may be complementarily conically shaped so that when jaws 118 and 120 are disposed in a closed position they form a substantially sharp obturator tip to facilitate the penetration or dissection of tissue. It will be understood that other profile shapes for jaws 118 and 120 may be used in connection with the invention, e.g., square, rhomboidal, or any other combination of flat surfaces and angled corners capabable of tissue penetration.

In use, instrument 100 is guided to the wall of an anatomical cavity, with jaws 118 and 120 in a closed position. Instrument 100 is advanced distally through the abdominal wall with jaws 118 and 120 acting as a trocar to pierce and separate the tissue of the abdominal wall. Once the abdominal wall has been pierced by instrument 100, the instrument can be manipulated externally of the body to position jaws 118 and 120 adjacent to an operative site. Various grasping and/or cutting functions can be performed at the operative site using different portions of the jaws and by operating the handles of the instrument to open and close the jaws. It will be understood that the inner surfaces of jaws 118 and 120 may include blades, teeth, indentations, or the like that are adapted for use in laparoscopic surgical procedures. It will also be understood that both laparoscopic instruments 10 and 100 allow for easier axial manipulation, and at shallower angles relative to the surface of the anatomical cavity, than with prior art laparoscopic instruments. Further, the axial movement of instruments 10 and 100 is enhanced due to the low coefficient of friction between the outer surface of outer tubular member 14 and the edges of the incision.

Figure 5:
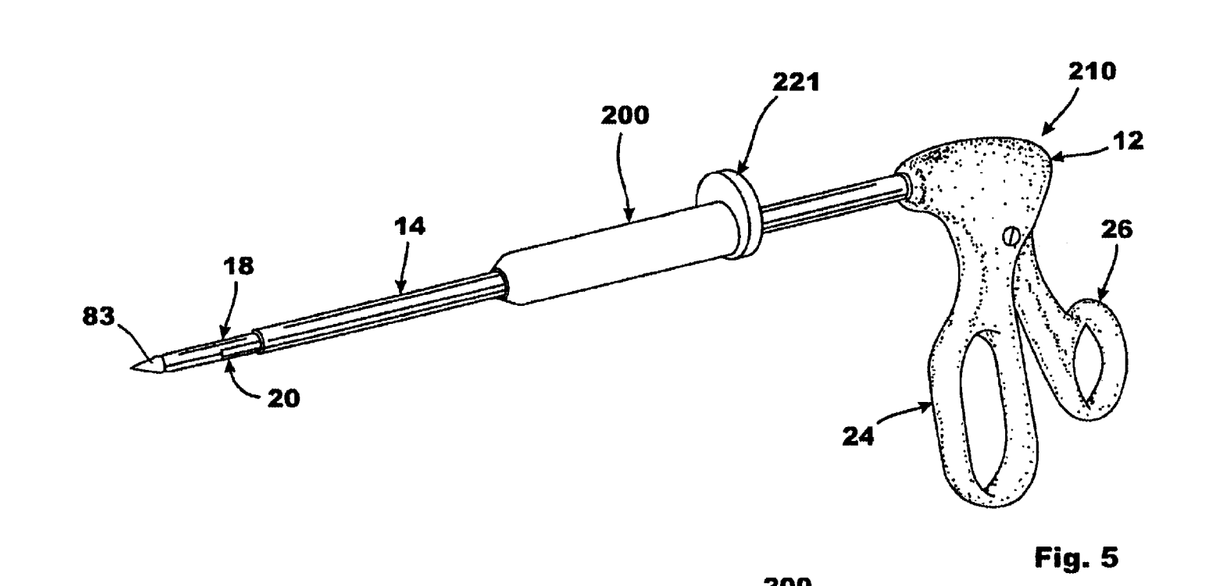
FIG. 5 is an elevational view of an endoscopic instrument according to another alternative embodiment of the present invention including an optional use portal sleeve.
Figure 6:
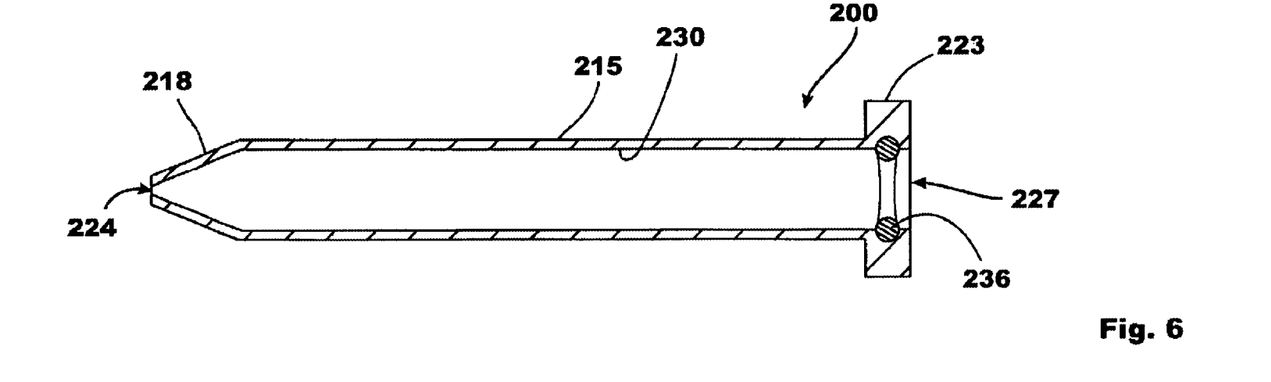
FIG. 6 is a cross-sectional view of the optional use portal sleeve shown in FIG. 5, as taken along line 6—6 in FIG. 5.

Referring to FIGS. 5 and 6, a further alternative embodiment of the present invention provides an optional portal 200 that is slidably and sealingly positioned over a portion of outer tubular member 14 of instrument 210. More particularly, portal 200 comprises an elongate cannula 215, a frusto-conical tip 218, and a hub 221. Cannula 215 is formed from a relatively rigid, biocompatible metal or polymer material, and defines a distal opening 224, a proximal opening 227, and a longitudinally extending lumen 230 that communicates with both openings. Frusto-conical tip 218 is formed on the distal end of cannula 215 and surrounds distal opening 224. Hub 221 projects radially outwardly from the proximal end of cannula 215 to form an annular shoulder 233. An o-ring seal 236 is positioned within lumen 230, adjacent to proximal opening 227, and in concentric relation to hub 221. O-ring seal 236 comprises an inner diameter that is smaller than the diameter of outer tubular member 14, and is securely fastened to the inner surface of cannula 215 so as to be fixed in place.

Portal 200 is positioned on the outer surface of outer tubular member 14 by simply orienting instrument 210 so that the jaws are positioned in coaxial confronting relation with proximal opening 227. Once in this position, instrument 210 is moved toward portal 200 so that the jaws enter proximal opening 227 and lumen 230. As this occurs, o-ring seal 236 sealingly engages outer tubular member 14, and slides along its surface as portal 200 is slid onto instrument 210.

If, during a laparoscopic procedure, a surgeon determines that a portal is required, he need only push on hub 221 with sufficient force to cause portal 200 to sealingly slide along outer tubular member 14 until frusto-conical tip 218 enters the abdominal wall through the previously created incision. O-ring seal 236 prevents gas leaking from the pneumoperitoneum through cannula 215. The outer surface of portal 200 is preferably textured to enhance engagement with the edges of the incision so as to promote the sealing and anchoring of portal 200 within the pneumoperitoneum. Portal 200 allows for easy instrument exchange by the surgeon.

Figure 7:
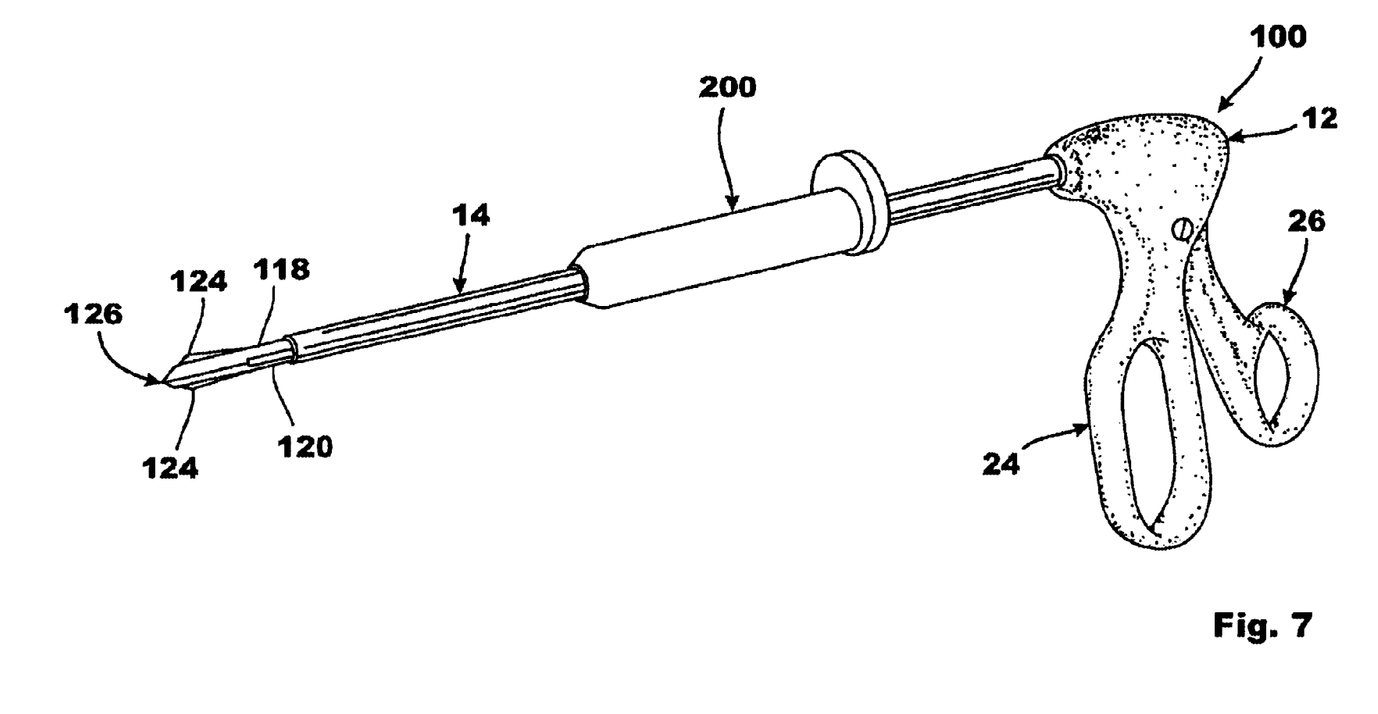
FIG. 7 is an elevational view of an endoscopic instrument according to a further alternative embodiment of the present invention.

FIGS. 5 and 7 show embodiments of the present invention wherein a releasable trocar 83 or a pair of jaws 118 and 120 forming a pair of blunt-edged blades or tissue separators are combined with a portal 200.

It is to be understood that the present invention is by no means limited only to the particular constructions herein disclosed and shown in the drawings, but also comprises any modifications or equivalents within the scope of the claims.

What is claimed is:

1. A surgical instrument for use in performing endoscopic procedures within an anatomical cavity comprising:

a handle; and an elongate tubular member having a proximal end coupled with said handle for being disposed externally of the anatomical cavity and a distal end for being disposed within the anatomical cavity and carrying a pair of opposed, relatively movable jaws;

each said jaw defining (i) a functional portion on the inner surface of the jaw; and (ii) a blunt-edge tissue separator that projects outwardly from the outer surface of the jaw;

wherein distal tips of the jaws are shaped for piercing, separating, and penetrating tissue when the jaws are closed;

and the blunt-edge tissue separators comprise blunt-edge blades arranged circumferentially in spaced relation on opposite jaws;

so that when the jaws are in a closed position they may be used for tissue penetration when applied to the tissue with axial force, and functional portions are operable to converge and diverge by manipulation of said handle.

2. The surgical instrument according to claim 1 wherein the jaws, when closed, are adapted to pierce, separate, and penetrate tissue.

3. The surgical instrument according to claim 2 wherein said tissue comprises skin and/or wall of an anatomical cavity or surgical site.

4. The surgical instrument of claim 3 wherein the distal tips of the jaws are complementarily generally rounded or conically shaped when closed to form a substantially sharp oburator tip to penetrate or dissect tissue.

5. The surgical instrument of claim 1 wherein the blunt-edge tissue separator comprises an outer contour, shape or projection adapted to penetrate tissue upon axial force and movement of the instrument relative the tissue.

6. The surgical instrument of claim 5 wherein the outer contour, shape or projection comprises a combination of flat and angled corners capable of tissue penetration.

7. The surgical instrument of claim 1 further comprising one or more functional portions on the inner surface of a jaw.

8. The surgical instrument of claim 7 wherein the functional portion is a blade, tooth, or indentation.

9. A surgical instrument according to claim 1 wherein said jaws cooperate to define a grasping portion at a distal end having opposed inner surfaces.

10. A surgical instrument according to claim 9 wherein said grasping means includes a combination of indentations that are arranged in a pattern on said inner surfaces of said jaws.

11. The surgical instrument of claim 1 further comprising:

a portal tube sealingly positioned on said elongate tubular member and operative thereon to move between (i) a first position in which said portal is in a proximal location on said elongate tubular member and in spaced relation to said anatomical cavity, and (ii) a second position in which said portal is in a distal location on said elongate member and in scaled communication with said anatomical cavity.

12. A surgical instrument according to claim 11 wherein said portal is slidably positioned over a portion of said elongate member.

13. A surgical instrument according to claim 11 wherein said portal comprises an elongate cannula having a distal opening, a proximal opening, and a longitudinally extending lumen that communicates with both openings, a frusto-conical tip formed on a distal end of said cannula and surrounding said distal opening, and a hub projecting radially outwardly from a proximal end of said cannula, and including an o-ring seal positioned within said lumen, adjacent to said proximal opening, and in concentric relation to said hub, said o-ring defining an inner diameter that is smaller than the diameter of said elongate member.

14. The surgical instrument of claim 1 wherein said blunt-edge tissue separator comprises a blunt-edge blade.

15. The surgical instrument of claim 1 further comprising a second blunt-edge tissue separator on the opposite jaw.

16. The surgical instrument of claim 15 wherein the blunt-edge blades project outwardly from the jaws.

* * * * *